US012570590B2

(12) United States Patent
Kushida et al.

(10) Patent No.: US 12,570,590 B2
(45) Date of Patent: Mar. 10, 2026

(54) METHOD FOR MANUFACTURING 2-CHLORO-1, 1-DIFLUOROETHANE (HCFC-142), 1,1,2-TRIFLUOROETHANE (HFC-143), AND (E)-1,2-DIFLUOROETHYLENE (HFO-1132(E)) AND/OR (Z)-1,2-DIFLUOROETHYLENE (HFO-1132(Z))

(71) Applicant: DAIKIN INDUSTRIES, LTD., Osaka (JP)

(72) Inventors: Megumi Kushida, Osaka (JP); Kazuhiro Takahashi, Osaka (JP); Tsubasa Nakaue, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 577 days.

(21) Appl. No.: 18/089,024

(22) Filed: Dec. 27, 2022

(65) Prior Publication Data

US 2023/0138340 A1 May 4, 2023

Related U.S. Application Data

(63) Continuation of application No. PCT/JP2021/025945, filed on Jul. 9, 2021.

(30) Foreign Application Priority Data

Jul. 10, 2020 (JP) ................................. 2020-119061

(51) Int. Cl.
*C07C 17/25* (2006.01)

(52) U.S. Cl.
CPC .................................... *C07C 17/25* (2013.01)

(58) Field of Classification Search
CPC ..... C07C 17/25; C07C 17/206; C07C 17/087; C07C 19/12; C07C 19/08
See application file for complete search history.

(56) References Cited

U.S. PATENT DOCUMENTS

| | | | |
|---|---|---|---|
| 3,432,562 A * | 3/1969 | Gardner | .................. C07C 17/25 |
| | | | 570/156 |
| 4,804,493 A | 2/1989 | Gorski | |

| | | | |
|---|---|---|---|
| 5,569,794 A | 10/1996 | Tung | |
| 5,714,651 A | 2/1998 | Elsheikh et al. | |
| 2002/0183569 A1 | 12/2002 | Bolmer et al. | |
| 2003/0018225 A1 | 1/2003 | Klausmeyer | |
| 2009/0030244 A1 | 1/2009 | Merkel et al. | |
| 2012/0117990 A1 | 5/2012 | Rached et al. | |
| 2014/0330051 A1 | 11/2014 | Lui et al. | |
| 2017/0267612 A1 | 9/2017 | Bonnet et al. | |
| 2019/0040292 A1 | 2/2019 | Rached et al. | |
| 2021/0163381 A1 | 6/2021 | Komatsu | |
| 2022/0119694 A1 | 4/2022 | Rached et al. | |

FOREIGN PATENT DOCUMENTS

| | | |
|---|---|---|
| JP | 1-128945 | 5/1989 |
| JP | 1-132539 | 5/1989 |
| JP | 1-265042 | 10/1989 |
| JP | 2-150499 | 6/1990 |
| JP | 2004-534060 | 11/2004 |
| JP | 2008-524433 | 7/2008 |
| JP | 2010-534680 | 11/2010 |
| JP | 2013-500373 | 1/2013 |
| JP | 2014-534899 | 12/2014 |
| JP | 2017-501992 | 1/2019 |
| JP | 2019-196312 | 11/2019 |
| WO | 2006/069362 | 6/2006 |

OTHER PUBLICATIONS

Chen et al. CN 103709009 abstract only (Year: 2014).*
International Preliminary Report on Patentability and Written Opinion of the International Searching Authority issued Jan. 10, 2023 in International (PCT) Application No. PCT/JP2021/025945.
Extended European Search Report issued Jul. 8, 2024 in corresponding European Patent Application No. 21838009.5.
International Search Report (ISR) issued Sep. 28, 2021 in International (PCT) Application No. PCT/JP2021/025945.

* cited by examiner

*Primary Examiner* — Jafar F Parsa
(74) *Attorney, Agent, or Firm* — Wenderoth, Lind & Ponack, L.L.P.

(57) ABSTRACT

An object of the present disclosure is to provide a method for producing HCFC-142, which is a target product, with high yield and high efficiency, by preventing the decomposition of starting materials, such as HCC-140 and HCO-1130. A method for producing HCFC-142, comprising bringing a chlorine-containing compound into contact with hydrogen fluoride in the presence of a stabilizer to perform at least one fluorination reaction, thus obtaining a reaction gas containing HCFC-142, hydrogen chloride, and hydrogen fluoride.

9 Claims, No Drawings

1

METHOD FOR MANUFACTURING 2-CHLORO-1, 1-DIFLUOROETHANE (HCFC-142), 1,1,2-TRIFLUOROETHANE (HFC-143), AND (E)-1,2-DIFLUOROETHYLENE (HFO-1132(E)) AND/OR (Z)-1,2-DIFLUOROETHYLENE (HFO-1132(Z))

TECHNICAL FIELD

The present disclosure relate to a method for producing 2-chloro-1,1-difluoroethane (HCFC-142), 1,1,2-trifluoroethane (HFC-143), and (E)-1,2-difluoroethylene (HFO-1132 (E)) and/or (Z)-1,2-difluoroethylene (HFO-1132(Z)).

BACKGROUND ART

Various conventional methods have been proposed for the production of fluoroethane, such as HCFC-142.

Patent Literature 1 discloses a method for producing HCFC-142 from 1,1,2-trichloroethane (HCC-140) and/or 1,2-dichloroethylene (HCO-1130).

Patent Literature 2 discloses a heat transfer composition containing an iodocarbon and a diene-based compound for stabilizing the decomposition of the iodocarbon.

CITATION LIST

Patent Literature

PTL 1: JP2017-501992A
PTL 2: JP2008-52433A

SUMMARY

The present disclosure includes the following aspects.
Item 1
A method for producing 2-chloro-1,1-difluoroethane (HCFC-142) comprising
bringing at least one chlorine-containing compound selected from the group consisting of 1,1,2-trichloroethane (HCC-140), (E)-1,2-dichloroethylene (HCO-1130(E)), (Z)-1,2-di-chloroethylene (HCO-1130(Z)), 1,2-dichloro-1-fluoroethane (HCFC-141), (E)-1-cloro-2 fluoroethylene (HCFO-1131 (E)) and (Z)-1-chloro-2-fluoroethylene (HCFO-1131(Z)) into contact with hydrogen fluoride in the presence of a stabilizer to perform at least one fluorination reaction, thus obtaining a reaction gas containing HCFC-142 hydrogen chloride, and hydrogen fluoride.

In the present specification, terms are abbreviated as follows.
1,1,2-trichloroethane: HCC-140
(E)- and/or (Z)-1,2-dichloroethylene: HCO-1130(E/Z)
(E)-1,2-dichloroethylene: HCO-1130(E)
(Z)-1,2-dichloroethylene: HCO-1130(Z)
1,2-dichloro-1-fluoroethane: HCFC-141
(E) and/or (Z)-1-chloro-2-fluoroethylene: HCO-1131(E/Z)
(E)-1-chloro-2-fluoroethylene: HCFO-1131(E)
(Z)-1-chloro-2-fluoroethylene: HCFO-1131(Z)
2-chloro-1,1-difluoroethane: HCFC-142
1,1,2-trifluoroethane: HFC-143
(E)- and/or (Z)-1,2-difluoroethylene: HFO-1132(E/Z)
(E)-1,2-difluoroethylene (HFO-1132(E))
(Z)-1,2-difluoroethylene (HFO-1132(Z))
"(E/Z)" above means that the E (trans) and/or Z (cis) bodies are included.

In the present disclosure, the pressure is gauge pressure unless indicated otherwise.

Advantageous Effects of Invention

According to the method for producing HCFC-142 of the present disclosure, the decomposition of a starting material, such as HCC-140 and HCO-1130, is suppressed, thus producing HFC-142 with high yield and high efficiency.

DESCRIPTION OF EMBODIMENTS

It is known that HCC-140 ($CH_2ClCHCl_2$) and HCO-1130 (E/Z) (CHCl=CHCl), which are starting materials for the production of HCFC-142, easily decompose, and the decomposition causes hydrogen chloride (HCl) to generate. For this reason, care must be taken in handling starting materials of HCC-140 and HCO-1130 (E/Z).

The present inventors have found that the decomposition of such HCC-140, HCO-1130 (E/Z), and the like affects conversion and selectivity in the production of HCFC-142.

The method for producing 2-chloro-1,1-difluoroethane (HCFC-142) of the present disclosure comprises bringing at least one chlorine-containing compound selected from the group consisting of 1,1,2-trichloroethane (HCC-140), (E)-1,2-dichloroethylene (HCO-1130(E)), (Z)-1,2-dichloroethylene (HCO-1130(Z)), 1,2-dichloro-1-fluoroethane (HCFC-141), (E)-1-chloro-2-fluoroethylene (HCFO-1131(E)), and (Z)-1-chloro-2-fluoroethylene (HCFO-1131(Z)) into contact with hydrogen fluoride in the presence of a stabilizer to perform at least one fluorination reaction, thus obtaining a reaction gas containing HCFC-142, hydrogen chloride, and hydrogen fluoride.

The method for producing HCFC-142 of the present disclosure having the above feature prevents the decomposition of starting materials, such as HCC-140 and HCO-1130, extends the catalyst life when a catalyst is used, and prevents the formation of by-products, thus producing HCFC-142 with high yield and high efficiency.

(1) Starting Material Compound

In the production method of the present disclosure, at least one chlorine-containing compound selected from the grout consisting of HCC-140, HCO-1130 (E/Z), HCFC-141, and HCFO-1131 (E/Z) is used as a starting material compound.

"(E/Z)" above means that the E (trans) and/or Z (cis) bodies are included.

All of these chlorine-containing compounds are available at low cost, which can reduce the costs for the HCFC-142 production method.

Among these chlorine-containing compounds, the chlorine-containing compound is preferably HCC-140 or HCO-1130 (E/Z), or both, and more preferably HCO-1130 (E/Z), from the viewpoint of the costs for the starting material.

(2) Stabilizer

In the production method of the present disclosure, the chlorine-containing compound described above is brought into contact with hydrogen fluoride in the presence of a stabilizer. The use or the stabilizer prevents the decomposition of chlorine-containing compounds, such as HCC-140 and HCO-1130 (E/Z), which are starting materials, extends the catalyst life when a catalyst is used, and suppresses the generation of by-products, which allows the production of HCFC-142 with nigh efficiency and high yield.

As the stabilizer, at least one stabilizer selected from the group consisting of hydroquinone stabilizers, unsaturated alcohol stabilizers, nitro stabilizers, amine stabilizers, phenol stabilizers, epoxy stabilizers, and other stabilizers can be preferably used.

As a hydroquinone stabilizer, at least one hydroquinone stabilizer selected from the group consisting of hydroquinone monomethyl ether (MEHQ), methoxyhydroquinone, and methylhydroquinone can be preferably used.

As an unsaturated alcohol stabilizer, at least one unsaturated alcohol stabilizer selected from the group consisting of 3-butene-2-ol, 2-butene-1-ol, 4-propene-1-ol, 1-propene-3-ol, 2-methyl-3-butene-2-ol, 3-methyl-3-butene-2-ol, 3-methyl-2-butene-1-ol, 2-hexen-1-ol, 2,4-hexadiene-1-ol, and oleyl alcohol can be preferably used.

As a nitro stabilizer, at least one nitro stabilizer selected from the group consisting of aliphatic nitro compounds such as nitromethane, nitroethane, 1-nitropropropane, and 2-nitropropropane; and aromatic nitro compounds such as nitrobenzene, o-, m- or p-dinitrobenzene, o-, m- or p-nitrotoluene, dimethylnitrobenzene, m-nitroacetophenone, o-, m- or p-nitrophenol, o-nitroanisole, m-nitroanisole, and p-nitroanisole, can b preferably used.

As an amine stabilizer, at least one amine stabilizer selected from the group consisting of pentylamine, hexylamine, diisopropylamine, diisobutylamine, di-n-propylamine, diallylamine, N-methylaniline, pyridine, morpholine, N-methylmorpholine, triallylamine, allylamine, α-methylbenzylamine, dimethylamine, trimethylamine, ethylamine, diethylamine, triethylamine, propylamine, isopropylamine, dipropylamine, tripropylamine, butylamine, isobutylamine, dibutylamine, tributylamine, dibentylamine tribentylamine, 2-ethylhexylamine, aniline, N,N-dimethylaniline, N,N-diethylaniline ethylenediamine, propylenediamine, diethylenediamine, tetraethylenepentamine, benzylamine, dibenzylamine, diphenylamine, and diethylhydroxylamine can be preferably used.

As a phenolic stabilizer, at least one phenolic stabilizer selected from the group consisting of 2,6-ditertiary-butyl-4-methylphenol, 3-cresol, phenol, 1,2-benzenediol, 2-isopropyl-5-methylphenol, and 2-methoxyphenol can be preferably, used.

As an epoxy stabilizer, at least one epoxy stabilizer selected from the group consisting of butylene oxide, 1,2-propylene oxide, 1,2-butylene oxide, butyl glycidyl ether, diethylene glycol diglycidyl ether, and 1,2-epoxy-3-phenoxypropane can be preferably used.

As other stabilizers, at least one stabilizer selected from the group consisting of butylhydroxytoluene, butylhydroxyanisole, 2-propanol, and α-pinene can be preferably used.

The stabilizer is preferably at least one stabilizer selected from the group consisting of hydroquinone stabilizers, unsaturated alcohol stabilizers, nitro stabilizers, amine stabilizers, phenol stabilizers, and epoxy stabilizers; preferably at least one hydroquinone stabilizer selected from the group consisting of hydroquinone monomethyl ether (MEHQ), methoxyhydroquinone, and methylhydroquinone; and more preferably hydroquinone monomethyl ether (MEHQ).

The amount (content) of the stabilizer used is preferably about 10 ppm to 50,000 ppm, more preferably about 20 ppm to 1,000 ppm, even more preferably about 30 ppm to 500 ppm, and particularly preferably about 80 ppm to 115 ppm, as a weight ratio of the stabilizer to the above chlorine-containing compound (starting material compound).

Using the stabilizer in the above range prevents the decomposition of the chlorine-containing compound, such as HCC-140 and HCO-1130 (E/Z), as a starting material, extends the catalyst life when a catalyst is used, and prevents the formation of by-products, which allows the production of HCFC-142 with high yield and high efficiency.

(3) Fluorination Reaction

The production method of the present disclosure is characterized in that the method comprises bringing the above chlorine-containing compound into contact with hydrogen fluoride to perform at least one fluorination reactions, thereby obtaining reaction gas containing HCFC-142, hydrogen chloride, and hydrogen fluoride.

The at least one fluorination reaction performed with hydrogen fluoride may be a gas-phase reaction or a liquid-phase reaction. The fluorination reaction that is performed until HCFC-142 is obtained may be one fluorination reaction or two or more fluorination reactions, depending on the chlorine-containing compound for use.

In the present disclosure, unless otherwise specified, the pressure is a gauge pressure.

(3-1) Gas-Phase Reaction

In the production method of the present disclosure, the fluorination reaction is preferably performed in a gas phase.

In the case of a gas-phase reaction, it is sufficient if the chlorine-containing compound and the hydrogen fluoride both in their gas form come into contact with each other within the reaction temperature range described later. The chlorine-containing compound may be in liquid form when being supplied.

For example, a chlorine-containing compound in liquid form at room temperature under ordinary pressure is vaporized with a vaporizer, then allowed to pass through a preheating regio, and supplied to a mixing region in which the chlorine-containing compound is brought into contact with hydrogen fluoride, thereby performing a reaction in a gas phase. Alternatively, a chlorine-containing compound in liquid form may be supplied to a reactor, and vaporized when the chlorine-containing compound has reached a region within which the compound is reactive with the hydrogen fluoride to cause a reaction.

The hydrogen fluoride for use is preferably anhydrous hydrogen fluoride (hydrofluoric acid, hydrogen fluoride, HF), from the standpoint of suppressing the corrosion of the reactor or the degradation of the catalyst.

The method for vaporizing a chlorine-containing compound in a reaction region can be any method, and may be selected from a wide range of known methods. For example, the following method may be used. A reaction tube is filled with a material that is excellent in heat conductance, has no catalytic activity in a fluorination reaction, and is stable against hydrogen fluoride, such as nickel beads and Hastelloy pieces. The temperature distribution inside the reaction tube is then made uniform, and the reaction tube is heated to a temperature equal to or higher than the vaporization temperature of the chlorine-containing compound. The chlorine-containing compound in liquid form is supplied to the reactor tube and vaporized so as to transform it into a gas phase.

The method for supplying hydrogen fluoride to a reactor can be any method. For example, hydrogen fluoride in a gas phase can be supplied to a reactor together with a chlorine-containing compound.

Molar Ratio of Hydrogen Fluoride Relative to Chlorine-Containing Compound

In the production method of the present disclosure, the molar ratio of the hydrogen fluoride to the chlorine-containing compound (1 mol) in the fluorination reaction is preferably 1 or more, more preferably 5 or more, and still more preferably 10 or more. The upper limit of the molar ratio is, although not limited to his, preferably about 60 from the standpoint of energy costs and productivity.

A molar ratio within these ranges enables both the chlorine-containing compound conversion and/or HCFC-142 selectivity to be maintained within a more efficient (excellent) range than with conventional methods.

In the present specification, "conversion" refers to the proportion (mol %) of the total mol of compounds other than the (chlorine-containing) compounds (starting material compounds) described above contained in outflow gas (i.e., reaction gas) coming from the outlet of the reactor relative to the mol of the chlorine-containing compound (starting material compound) supplied to the reactor.

In the present specification, "selectivity" refers to the proportion (mol %) of the mol of the target compound (HCFC-142) contained in outflow gas (i.e., reaction gas) coming from the outlet of the reactor relative to the total mol of the compounds other than the chlorine-containing compounds (starting material compounds) described above.

In a fluorination reaction in a gas phase, the chlorine-containing compound as a starting material compound may be supplied to a reactor as is, or the chlorine-containing compound may be diluted with an inert gas such as nitrogen, helium, or argon, and then supplied to the reactor.

Catalyst

In the production method of the present disclosure, the fluorination reaction is preferably performed in the presence of a catalyst.

A fluorination reaction in the presence of a catalyst in a gas phase can use any known gas-phase fluorination catalyst selected from a wide range of such catalysts. Examples include oxides, hydroxides, halides, halogen oxides, and inorganic salts of chromium, aluminum, cobalt, manganese, nickel, or iron; and mixtures thereof.

Of these, in order to increase the conversion of the chlorine-containing compound, chromium-based catalysts such as $CrO_2$, $Cr_2O_3$, $FeCl_3/C$, $Cr_2O_3/Al_2O_3$, $Cr_2O_3/AlF_3$, $Cr_2O_3/C$, and $CoCl_2/Cr_2O_3$ are preferable for use.

The chromium oxide/aluminum oxide-based catalysts for use are preferably those disclosed in U.S. Pat. No. 5,155, 082, specifically a chromium oxide/aluminum oxide catalyst (e.g., $Cr_2O_3/Al_2C_3$), and those obtained by combining a halide of cobalt, nickel, manganese, rhodium, or ruthenium with such a chromium oxide/aluminium oxide catalyst.

The catalyst for use may be a partly or entirely crystallized catalyst, or an amorphous catalyst. The crystallizability can be suitably selected. For example, chromium oxide with a variety of particle sizes is commercially available. To control the particle size and crystallizability, a metallic catalyst may be prepared by precipitating chromium hydroxide from chromium nitrate and ammonia, and burning the precipitate.

The catalyst for use mar be a single catalyst, or a mixture of two or more catalysts. As the mixture, a mixture of a purchased or prepared catalyst with a catalyst having a different preparation method or composition can be used.

The carrier for use may be, for example, a variety of activated carbon, magnesium oxide, zirconia oxide, or alumina.

These catalysts may be subjected to fluorination treatment using, for example, anhydrous hydrogen fluoride (hydrofluoric acid, hydrogen fluoride, HF) or a fluorine-containing compound before they are used in a fluorination reaction. In particular, these catalysts are preferably subjected to fluorination treatment using anhydrous hydrogen fluoride.

Reaction Temperature in Gas-Phase Fluorination Reaction

In the production method of the present disclosure, the reaction temperature in a gas-phase fluorination reaction as a temperature in side the reactor is preferably about 150 to 600° C., more preferably about 200 to 500° C., and still more preferably about 230 to 400° C. Setting the reaction temperature to about 150° C. or more can improve the selectivity for a target product. A reaction temperature or about 600° C. or less can reduce the risk that carbides are formed by the reaction, and that the carbides adhere to and/or accumulate on the reaction tube wall or on the filler to gradually block the reactor.

If such a risk is involved, carbides remaining in the reaction tube can be removed through combustion by entraining oxygen into the reaction system, or by temporarily stopping the reaction to allow oxygen or air to circulate.

Oxygen Concentration of Gas-Phase Fluorination Reaction

In the production method of the present disclosure, the oxygen concentration in the fluorination reaction is preferably about 0.1 mol % to 30 mol %, preferably about 0.5 mol % to 20 mol %, and still more preferably about 1 mol % to 15 mol %, relative to the chlorine-containing compound of the starting material compound.

Reaction Pressure in Gas-Phase Fluorination Reaction

The reaction pressure in a gas-phase fluorination reaction can be any pressure under which a chlorine-containing compound and hydrogen fluoride can be present in their gas phase. The reaction pressure can be an ordinary pressure, increased pressure, or decreased pressure. For example, the reaction can be performed under reduced pressure or atmospheric pressure (0 MPaG); the reaction can also be performed under increased pressure as long as the starting materials do not transform into liquid. Typically, the reaction pressure is preferably within the range of 0 to 2 MPaG, and more preferably 0.2 to 1 MPaG.

Reaction Time for Gas-Phase Fluorination Reaction

In the production method of the present disclosure, the reaction time for the gas-phase fluorination reaction can be any time. Typically, the contact time represented by W/Fo (the ratio of the catalyst added W (g) to the total flow rate Fo (flow rate at C under 0 MPaG:cc/sec) of the starting material gas that is allowed to flow in a reaction system) is preferably about 0.1 to 100 g·sec/cc, and more preferably about 5 to 50 g·sec/cc.

The total flow rate of the starting material gas in this case refers to the sum of the total flow rate of the chlorine-containing compound and the hydrogen fluoride (starting materials), and the flow rate of inert gas, oxygen, or the like when such an optional component is added.

(3-2) Liquid Phase Reaction

In the product on method of the present disclosure, the liquid-phase catalyst for use in performing a fluorination reaction in the presence of a catalyst in a liquid phase can be any catalyst. Specifically, the liquid-phase catalyst for use may be at least one member selected from the croup consisting of Lewis acid, transition metal halides, transition metal oxides, halides of the metals of group Ivb, and halides of the metals of group Vb.

Under liquid phase reaction, the catalyst for use may be at least one member selected from the group consisting of antimony halides, tin halides, tantalum halides, titanium halides, niobium halides, molybdenum halides, iron halides, halogenated chromium fluoride, and oxidized chromium fluoride.

More specifically, the liquid-phase catalyst for use is preferably $SbCl_5$, $SbCl_3$, $SbF_5$, $SnCl_4$, $TaCl_5$, $TiCl_4$, $NbCl_5$, $MoCl_6$, and $FeCl_3$; and those prepared from a chloride salt and hydrogen fluoride, such as $SbCl_{(5-y)}F_y$, $SbCl_{(3-y)}$ $F_y$, $SnCl_{(4-y)}F_y$, $TaCl_{(5-y)}F_y$, $TiCl_{(4-y)}F_y$, $NbCl_{(5-y)}F_y$, $MoCl_{(6-y)}$ $F_y$, and $FeCl_{(3-y)}F_y$ (the lower limit or y is 0.1 or more, and the upper limit of y is equal to or lower than the valence of individual elements).

These catalysts can be used singly, or in a combination of two or more.

Of these, antimony-based catalyst are preferable, and antimony pentachloride is particularly preferable.

These catalysts can be easily renewed by a known technique when they have become inactive. A usable method for renewing such a catalyst is bringing chlorine into contact with the catalyst. For example, chlorine in an amount of about 0.15 to 25 g/hr may be added per 100 g of a liquid-phase fluorination catalyst in a liquid-phase reaction.
Reaction Temperature in Liquid-Phase Fluorination Reaction In the production method of the present disclosure, the reaction temperature in a liquid-phase fluorination reaction as a temperature inside a reaction system is preferably about 50 to 200° C., and more preferably about 80 to 150° C. Setting the reaction temperature to 50° C. or more can increase the selectivity for a target product and productivity.
Pressure in Liquid-Phase Fluorination Reaction In the production method of the present disclosure, the pressure in a liquid-phase fluorination reaction is preferably within the range of 0 to 2 MPaG, and more preferably 0.2 to 1 MPaG as in a gas-phase reaction.
(3-3) Reactor In the production method of the present disclosure, the form of the reactor for use can be any form; the reactor for use can be selected from a wide range of known reactors. For example, tube-form flow reactor filled with a catalyst can be used. In a reaction in the absence of a catalyst, the reactor for use can be, for example, an adiabatic reactor with a void-tower, or an adiabatic reactor filled with a porous or non-porous metal or medium for increasing the degree of mixture of the hydrogen fluoride and the starting material in their gas phase. Alternatively, the reactor for use is preferably, for example, a multi-tube reactor from which heat is removed by using a heat medium and/or whose temperature distribution is made uniform.

In the use of a reactor with a void-tower, for example, the relationship between the flow rate of a chlorine-containing compound and the inner diameter of a reaction tube is preferably set such that the linear velocity is high and the heat-transfer area is large in order to improve heat-transfer efficiency using a reaction tube with a small inner diameter.

The reactor for use in both the gas-phase fluorination reaction and the liquid-phase fluorination reaction can be any reactor and can be selected from a wide range of known reactors. Specifically, the reactor for use is preferably one formed of a material that is resistant to corrosive action by hydrogen fluoride, such as Hastelloy, Inconel, Monel, or Incoloy.
(4) Recycling Step After a reaction gas comprising HCFC-142, hydrogen chloride, and hydrogen fluoride is obtained by the production method of the present disclosure, HCFC-142 can be obtained by various known separation methods. Hydrogen fluoride can also be recycled for fluorination reaction.

In the present disclosure, in order to recover a composition having a high proportion of HCFC-142 (target compound), after at least one chlorine-containing compound (starting material compound) selected from the group consisting of the HCC-140, HCO-1130 (E/Z), HCFC-141, and HCFO-1131 (E/Z)) is brought into contact with hydrogen fluoride in the presence or a stabilizer to perform at least one fluorination reaction, the chlorine-containing compound (starting material compound) can be recovered and recycled to the reaction.

In the present disclosure, after the chlorine-containing compound (starting material compound) is brought into contact with hydrogen fluoride (HF) in the presence of a stabilizer, a stream mainly comprising hydrogen chloride (HCl) produced after the reaction is first separated from the reaction gas, then a stream comprising the chlorine-containing compound (starting material compound) as the main component (sometimes comprising a stabilizer) is separated, and then a stream mainly comprising HCFC-142 (target compound) is separated, to recover HCFC-142.

The present disclosure preferably includes recycling at least one stream (containing a stabilizer) mainly containing the separated chlorine-containing compound (starting material compound) to the reaction, and again bringing the stream into contact with hydrogen fluoride (HF) in the presence of a stabilizer. (If necessary, the stabilizer can be added.) In the present disclosure, HCFC-142 (target compound) can be preferably recovered repeatedly to obtain a composition with a higher percentage of the target compound.
Method Comprising Recycling by the Method for Producing HCO-1130(E) from HCFC-142

The method for producing HCFC-142 of the present disclosure includes the step of bringing HCO-1130(E) (chlorine-containing compound) into contact with hydrogen fluoride in the presence of a stabilizer to obtain a reaction gas containing HCFC-142, hydrogen chloride, and hydrogen fluoride.

The method for producing HCFC-142 of the present disclosure preferably comprises the step of first separating a stream mainly comprising hydrogen chloride (HCl) produced after the reaction from a reaction gas, subsequently separating a stream of which the main component (sometimes comprising a stabilizer) is HCO-1130 CE) (chlorine-containing compound or a starting material compound), and subsequently separating a stream mainly comprising HCFC-142 (target compound), and recovering the HCFC-142.

The method for producing HCFC-142 of the present disclosure preferably includes recycling at least a portion of a stream (comprising a stabilizer) containing HC-1130(E) (chlorine-containing compound of a starting material compound) as a main component to the reaction, bringing the stream into contact with hydrogen fluoride in the presence of the stabilizer (if necessary, adding a stabilizer) in the presence of a stabilizer, to perform an least one fluorination reaction, thus obtaining a reaction comprising HCFC-142, hydrogen chloride, and hydrogen fluoride.
(5) Target Compound The method for producing HCFC-142 of the present disclosure comprises bringing the chlorine-containing compound into contact with hydrogen fluoride in the presence of a stabilizer to perform at least one fluorination reaction, thus obtaining a reaction gas containing HCFC-142, hydrogen chloride, and hydrogen fluoride. The obtained HCFC-142 can be used for various applications after purification treatment, it necessary.

In the HCFC-142 production method of the present disclosure, the use of the stabilizer prevents the decomposition of chlorine-containing compounds, such as HCC-140 and HCO-1130(E/Z), which are starting materials, extends the catalyst life when a catalyst is used, and suppresses the generation of by-products, which allows the production of HCFC-142 with high efficiency and high yield.

HCFC-142 can be preferably used as a starting material for the production of various refrigerants. HCFC-142 can also be preferably used as a starting material such as HFC-143 and HFO-1132 (E/Z).

The present disclosure further includes the production method of HFC-143, and production method of HFO-1132 (E) and/or HFO-1132(Z) (HFO-1132(E/Z)).

The production method of HFC-143 of the oresent disclosure comprises bringing HCFC-142 contained in the reaction gas obtained by the production method described above into contact with hydrogen fluoride to perform a fluorination reaction, thus obtaining HFC-143, hydrogen chloride, and hydrogen fluoride The production method of the HFC-143 is not particularly limited, and known methods can be widely used.

The method for producing HFO-1132(E) and/or HFO-1132(Z) (HFO-1132(E/Z)) of the present disclosure includes the step of subjecting HFC-143 contained in the reaction gas obtained by the production method to a dehydrofluorination reaction to obtain HFO-1132(E/Z).

The production method of HFO-1132(E/Z) is not particularly limited; however, a known method can be widely used.

According to various production methods of the present disclosure, the use of the stabilizer prevents the decomposition of chlorine-containing compounds, such as HCC-140 and HCO-1130, which are starting materials, extends the catalyst life when a catalyst is used, and prevents the generation of by-products, which allows the production of HCFC-142 with high efficiency and high yield. This further leads to the production of HFC-143 and HFO-1132 (E/Z) with high yield and high efficiency.

Embodiments of the present disclosure are described in more detail below with reference to Examples. However, the present disclosure is not limited to these Examples. Various modifications of the embodiments can be, of course, made without departing from the spirit and principal concept of the present disclosure.

Item 1

A method for producing 2-chloro-1,1-difluoroethane (HCFC-142), comprising
bringing at least one chlorine-containing compound selected from the group consisting of 1,1,2-trichloroethane (HCC-140), (E)-1,2 dichloroethylene (HCO-1130(E)), (Z)-1,2-dichloroethylene (HCO-1130(Z)), 1,2-dichloro-1-fluoroethane (HCFC-141), (E)-1-chloro-2 fluoroethylene (HCFO-1131(E)), and (Z)-1-chloro-2-fluoroethylene (HCFO-1131 (Z)) into contact with hydrogen fluoride in the presence of a stabilizer to perform at least one fluorination reaction, thus obtaining a reaction gas containing HCFC-142, hydrogen chloride, and hydrogen fluoride.

Item 2

The production method according to Item 1, wherein the stabilizer is at least one stabilizer selected from the group consisting of hydroquinone stabilizers, unsaturated alcohol stabilizers, nitro stabilizers, amine stabilizers, phenolic stabilizers, and epoxy stabilizers.

Item 3

The production method according to Item 1 or 2, wherein the molar ratio of the hydrogen fluoride to the chlorine-containing compound in the fluorination reaction is 1 or more.

Item 4

The production method according to any one of Items 1 to 3, wherein the fluorination reaction is performed in the presence of a catalyst.

Item 5

The production method according to Item 4, wherein the catalyst is at least a partly chromium-containing catalyst.

Item 6

The production method according to any one of Items 1 to 5, wherein the fluorination reaction is performed under pressure conditions of 0 MPaG to 2 MPaG.

Item 7

The production method according to Item 6, wherein the fluorination reaction is performed under temperature conditions of 150° C. to 600° C.

Item 8

The production method according to any one of Items 1 to 7, wherein the fluorination reaction is performed in a gas phase, and the contact time W/Fo between the chlorine-containing compound and the hydrogen fluoride is 0.1 g·sec/cc to 100 g·sec/cc.

Item 9

A method for producing 1,1,2-trifluoroethane (HFC-143), comprising further bringing HCFC-142 contained in the reaction gas obtained by the production method according to any one of Items 1 to 8 into contact with hydrogen fluoride to perform a fluorination reaction, thus obtaining a reaction gas containing HFC-143, hydrogen chloride, and hydrogen fluoride.

Item 10

A method for producing (E)-1,2-difluoroethylene (HFO-1132(E)) and/or (Z)-1,2-difluoroethylene (HFO-1132(Z)), comprising
subjecting the HFC-143 contained in the reaction gas obtained by the production method according to item 9 to a dehydrofluorination reaction.

EXAMPLES

Embodiments of the present disclosure are described in more detail below with reference to Examples. However, the present disclosure is not limited to the scope of the Examples.

(1) Preparation of Chromium Fluoride Oxide Catalyst

A chromium fluoride oxide catalyst was prepared in accordance with the following procedure.

First, chromium oxide represented by $Cr_xO_y$ was prepared in accordance with the method disclosed in JPH05-146680A. Specifically, 10% ammonia water was added to 765 g of a 5.7% aqueous chromium nitrate solution, and the thus-formed precipitate was recovered by filtration, followed by washing and then drying in air at 120° C. for 12 hours, thereby obtaining chromium hydroxide. This chromium hydroxide was then formed into pellets with a diameter of 3.0 mm and a height of 3.0 mm. The pellets were then burned in a nitrogen stream at 400° C. for hours, thereby obtaining chromium oxide. The obtained chromium oxide had specific surface area (according to the BET theory) of about 200 $m^2/g$.

Subsequently, the chromium oxide was subjected to fluorination treatment to obtain a chromium fluoride oxide catalyst.

Specifically, while a hydrogen fluoride-containing gas was allowed to flow into chromium oxide, the temperature was increased to 200 to 360° C. incrementally to heat the chromium oxide. After the temperature reached 360° C., fluorination was performed using hydrogen fluoride for 2 hours, thereby obtaining a chromium fluoride oxide catalyst ($Cr_2O_3$).

A tubular Hastelloy reactor with an inner diameter of 15 mm and a length of 1 m was then filled with 12 g of the obtained chromium fluoride oxide catalyst ($Cr_2O_3$).

The above reactor was maintained at 280° C. under a pressure of 0.6 MPaG (gauge pressure), and anhydrous hydrogen fluoride (HF, hydrofluoric acid, hydrogen fluoride) gas was supplied into the reactor at a flow rate of 9.3 mL/min (at a flow rate at 0° C. and 0.6 MPaG), and maintained for 1 hour.

(2) Production of HCFC-142 from HCO-1130 (E)

Gas-phase fluorination reaction
Starting material compound: (E)-1,2-dichloroethylene (HCO-1130(E))
Target compound: 2-chloro-1,1-difluoroethane (HCFC-142)

Example 1: Stabilizer: Presence of MvEHQ

In the reactor filled with the catalyst, CHCl=CHCl (HCO-1130(E)) comprising 80 ppm (weight ratio of a staring material compound (chlorine-containing compound) to HCO-1130 (E)) of hydroquinone monomethyl ether (MEHQ:hydroquinone monomethyl ether), which was a Example 2: Stabilizer: Presence of Diethyl Amine The gas-phase fluorination reaction was performed under the same conditions as in Example 1 above except that reaction conditions were such that diethylamine was used as a stabilizer and 10 ppm of diethylamine was contained as a weight ratio of the starting material compound (chlorine-containing compound) to HCO-1130(E).

After 50 hours from the start of the reaction, the conversion of HCO-1130((E) was 16%, the selectivity for HCFC-142 was 81%, and the selectivity for HFC-143 was 5.5%.

After 100 hours from the start of the reaction, the conversion of HCO-1130(E) was 12%, the selectivity for HCFC-142 was 80%, and the selectivity for HFC-143 was 3.9%.

Table 1 also shows the results of other components.

Comparative Example 1: Absence of Stabilizer

The gas-phase fluorination reaction was performed under the same conditions as in Example 1 above except that reaction conditions were such that the stabilizer was not used.

After 50 hours from the start of the reaction, the conversion of HCO-1130(E) was 15%, the selectivity for HCFC-142 was 71%, and the selectivity for HFC-143 was 1.3%.

After 100 hours from the start of the reaction, the conversion of HCO-1130(E) was 9%, the selectivity for HCFC-142 was 60%, and the selectivity for HFC-143 was 0.7%.

Table 1 also shows the results of other components.

TABLE 1

| | Gas-phase fluorination reaction | | Conversion (%) of starting material compound HCO-1130 (E) | Selectivity (%) of HCFC-141 | Selectivity (%) of HCFO-1131 (E) | Selectivity (%) of HCFC-142 | Selectivity (%) of HFC-143 |
|---|---|---|---|---|---|---|---|
| Example 1 | Presence of stabilizer MEHQ | After 50 hours | 16 | 2.1 | 7.4 | 83 | 5.8 |
| | | After 100 hours | 13 | 3.7 | 8.0 | 82 | 4.3 |
| Example 2 | Presence of stabilizer diethyl amine | After 50 hours | 16 | 2.3 | 7.5 | 81 | 5.5 |
| | | After 100 hours | 12 | 4.0 | 8.2 | 80 | 3.9 |
| Comparative Example 1 | Absence of stabilizer | After 50 hours | 15 | 3.3 | 7.5 | 71 | 1.3 |
| | | After 100 hours | 9 | 5.0 | 8.5 | 60 | 0.7 | starting material, was supplied at a flow rate of 0.92 mL/min (0° C., gas flow rate of 0.6 MPaG).

In the supply, the molar ratio of HF:HCO-1130(E) was 10:1. A gas containing oxygen ($O_2$) in an amount of 10 mol % relative to HC-1130(E) of the starting material compound (chlorine-containing compound) was used.

The contact time (W/Fo) was set to 10 g·sec/cc (g·sec·mL$^{-1}$).

After 50 hours from the start of the reaction, the conversion of HCO-1130 (E) was 16%, the selectivity for HCFC-142 was 83%, and the selectivity for HFC-143 was 5.8%.

After 100 hours from the start of the reaction, the conversion of HCO-1130(E) was 13%, the selectivity for HCFC-142 was 82%, and the selectivity for HFC-143 was 4.3%.

Table 1 shows the results of other components.

(3) Production of HCFC-142 from HCC-140

Gas-phase fluorination reaction
Starting material compound: 1,1,2-trichloroethane (HCC-140)
Target compound: 2-chloro-1,1-difluoroethane (HCC-142)

Example 3: Stabilizer: Presence of 2-Propanol

In the reactor filled with the catalyst, CHCl$_2$—CH$_2$Cl (HCC-140)) comprising 200 ppm (weight ratio of a staring material compound (chlorine-containing compound) to HCC-140) of 2-propanol, which was a stabilizer, was supplied at a flow rate of 0.92 mL/min (0° C., gas flow rate of 0.6 MPaG).

In the supply, the molar ratio of HF:HCC-140 was set to 10:1. A gas contain oxygen ($O_2$) in an amount of 10 mol %

13 relative to HCC-140 of the starting material compound (chlorine-containing compound) was used.

The contact time (W/Fo) was set to 10 g·sec/cc (g·sec·mL$^{-1}$).

After 50 hours from the start of the reaction, the conversion of HCC-140 was 95%, the selectivity for HCFC-142 was 22%, and the selectivity for HFC-143 was 0.2%.

After 100 hours from the start of the reaction, the conversion of HCC-140 was 90%, the selectivity for HCFC-142 was 20%, and the selectivity for HFC-143 was 0.2%.

Table 2 also shows the results of other components.

Example 4: Stabilizer: Presence of 1,2-Butylene Oxide

The gas-phase fluorination reaction was performed under the same conditions as in Example 3 above except that reaction conditions were such that 1,2-butylene oxide was used as a stabilizer and 500 ppm of 1,2-butylene oxide was contained as a weight ratio of the starting material compound (chlorine-containing compound) to HCC-140.

After 50 hours from the start of the reaction, the conversion of HCC-140 was 93%, the selectivity for HCFC-142 was 21%, and the selectivity for HFC-143 was 0.2%.

After 100 hours from the start of the reaction, the conversion of HCC-140 was 88%, the selectivity for HCFC-142 was 18%, and the selectivity for HFC-143 was 0.2%.

Table 2 also shows the results of other components.

Comparative Example 2: Absence of Stabilizer

The gas-phase fluorination reaction was performed under the same conditions as in Example 3 above except that the reaction conditions were such that the stabilizer was not used.

After 50 hours from the start of the reaction, the conversion of HCC-140 was 88%, the selectivity for HCFC-142 was 17%, and the selectivity for HFC-143 was 0.2%.

After 100 hours from the start of the reaction, the conversion of HCC-140 was 76%, the selectivity for HCFC-142 was 13%, and the selectivity for HFC-143 was 0.2%.

Table 2 also shows the results of other components.

14

(4) Discussion of Results

Comparing the results of the Examples with the results of the Comparative Examples indicates that by the addition of the stabilizer to the starting material of HCO-1130(E) or HCC-140 to perform a fluorination reaction, the conversion of HCO-1130(E) or HCC-140 is improved, and the selectivity (yield) of HCFC-142 and HFC-143 is improved.

The results indicate that the addition of a stabilizer to HCO-1130(E) or HCC-140 can suppress the degradation of the catalyst, and suppress the reduction of catalytic activity.

It can be evaluated that the addition of the stabilizer to HCO-1130(E) or HCC-140 (starting material compound) prevents the decomposition of HCO-1130(E) or HCC-140, thereby reducing the amount of HCl in the reaction system, thus improving the selectivity of HCFC-142 (target compound) and HFC-143 (next target compound).

Further, it can be evaluated that, by reducing the amount of HCl in the reaction system, the equilibrium of the reaction is biased to the fluorination side, specifically, HCFC-142 can be easily produced from HCO-1130(E) or HCC-140, or the intermediate product of HCFC-141, and thus, the selectivity of HCFC-142, which is the target compound, can be improved because.

The invention claimed is:

1. A method for producing 2-chloro-1,1-difluoroethane (HCFC-142), comprising bringing at least one chlorine-containing compound selected from the group consisting of 1,1,2-trichloroethane (HCC-140), (E)-1,2-dichloroethylene (HCO-1130(E)), (Z)-1,2-dichloroethylene (HCO-1130(Z)), 1,2-dichloro-1-fluoroethane (HCFC-141), (E)-1-chloro-2 fluoroethylene (HCFO-1131(E)), and (Z)-1-chloro-2-fluoroethylene (HCFO-1131(Z)) into contact with hydrogen fluoride in the presence of at least one stabilizer selected from the group consisting of hydroquinone stabilizers, unsaturated alcohol stabilizers, nitro stabilizers, amine stabilizers, phenolic stabilizers, epoxy stabilizers, and other stabilizers,

TABLE 2

| Gas-phase fluorination reaction | | | Conversion (%) of starting material compound HCC-140 | Selectivity (%) of HCFC-141 | Selectivity (%) of HCFO-1131 (E) | Selectivity (%) of HCFC-142 | Selectivity (%) of HFC-143 |
|---|---|---|---|---|---|---|---|
| Example 3 | Presence of stabilizer 2-propanol | After 50 hours | 95 | 5.8 | 1.7 | 22 | 0.2 |
| | | After 100 hours | 90 | 7.6 | 1.8 | 20 | 0.2 |
| Example 4 | Presence of stabilizer 1,2-butylene oxide | After 50 hours | 93 | 5.9 | 1.8 | 21 | 0.2 |
| | | After 100 hours | 88 | 7.9 | 1.8 | 18 | 0.2 |
| Comparative Example 2 | Absence of stabilizer | After 50 hours | 88 | 9.0 | 1.7 | 17 | 0.2 |
| | | After 100 hours | 76 | 11 | 1.8 | 13 | 0.2 | the other stabilizer being at least one stabilizer selected from the group consisting of butylhydroxytoluene, butylhydroxyanisole, 2-propanol, and α-pinene, to perform at least one fluorination reaction, thus obtaining a reaction gas containing HCFC-142, hydrogen chloride, and hydrogen fluoride.

2. The production method according to claim 1, wherein a molar ratio of the hydrogen fluoride to the chlorine-containing compound in the fluorination reaction is 1 or more.

3. The production method according to claim 1, wherein the fluorination reaction is performed in the presence of a catalyst.

4. The production method according to claim 3, wherein the catalyst is at least a partly chromium-containing catalyst.

5. The production method according to claim 1, wherein the fluorination reaction is performed under pressure conditions of 0 MPaG to 2 MpaG.

6. The production method according to claim 5, wherein the fluorination reaction is performed under temperature conditions of 150° C. to 600° C.

7. The production method according to claim 1, wherein the fluorination reaction is performed in a gas phase, and a contact time W/Fo between the chlorine-containing compound and the hydrogen fluoride is 0.1 g·sec/cc to 100 g·sec/cc.

8. A method for producing 1,1,2-trifluoroethane (HFC-143), comprising the steps of (i) conducting the method of claim 1 to produce HCFC-142, and (ii) further bringing HCFC-142 contained in the reaction gas obtained in step (i) into contact with hydrogen fluoride to perform a fluorination reaction, thus obtaining a reaction gas containing HFC-143, hydrogen chloride, and hydrogen fluoride.

9. A method for producing (E)-1,2-difluoroethylene (HFO-1132(E)) and/or (Z)-1,2-difluoroethylene (HFO-1132 (Z)), comprising the steps of (i) conducting the method of claim 8 to produce HCFC-143, and (ii) subjecting the HFC-143 contained in the reaction gas obtained in step (i) to a dehydrofluorination reaction.

* * * * *